US008750972B2

(12) United States Patent
Hofstadter et al.

(10) Patent No.: US 8,750,972 B2
(45) Date of Patent: *Jun. 10, 2014

(54) IMPLANTABLE MEDICAL DEVICE WITH AUTOMATIC SENSING ADJUSTMENT

(75) Inventors: Steve Hofstadter, Los Angeles, CA (US); Christopher Koch, Glendora, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 1282 days.

This patent is subject to a terminal disclaimer.

(21) Appl. No.: 12/560,008

(22) Filed: Sep. 15, 2009

(65) Prior Publication Data

US 2010/0049271 A1 Feb. 25, 2010

Related U.S. Application Data

(63) Continuation of application No. 11/366,929, filed on Mar. 1, 2006, now Pat. No. 7,610,090.

(51) Int. Cl.
*A61N 1/08* (2006.01)
(52) U.S. Cl.
USPC ............................... 600/509; 600/508; 607/2
(58) Field of Classification Search
USPC ............................................ 600/509; 607/28
See application file for complete search history.

(56) References Cited

U.S. PATENT DOCUMENTS

| 5,545,183 | A | 8/1996 | Altman |
| 6,782,291 | B1 | 8/2004 | Bornzin et al. |
| 7,006,869 | B2 | 2/2006 | Bradley |
| 7,610,090 | B1* | 10/2009 | Hofstadter et al. ............. 607/27 |
| 2003/0204232 | A1 | 10/2003 | Sommer et al. |
| 2004/0015197 | A1 | 1/2004 | Gunderson |
| 2004/0230243 | A1* | 11/2004 | Haefner et al. ................. 607/27 |
| 2006/0116730 | A1 | 6/2006 | Gunderson |
| 2007/0239047 | A1* | 10/2007 | Ghanem et al. ............... 600/509 |
| 2010/0114196 | A1* | 5/2010 | Burnes et al. .................... 607/4 |

OTHER PUBLICATIONS

NonFinal Office Action, mailed Dec. 22, 2008: Parent U.S. Appl. No. 11/366,929.
Final Office Action, mailed Jun. 10, 2009: Parent U.S. Appl. No. 11/366,929.
Notice of Allowance, mailed Aug. 21, 2009: Parent U.S. Appl. No. 11/366,929.

* cited by examiner

*Primary Examiner* — Carl H Layno
*Assistant Examiner* — Jennifer Ghand

(57) ABSTRACT

An implantable medical device system that senses physiologic processes via multiple sensor signal configurations. The device can further process the sensor configurations to obtain additional processed signal configurations. The device can utilize the processed configurations for ongoing sensing of the physiologic process. The device can also automatically evaluate the multiple sensor configurations as well as the processed configurations and select the configuration offering the best signal discrimination to reduce oversensing or erroneously interpreting secondary characteristics of the physiologic process as corresponding to primary characteristics of the process as in double-counting. The signal discrimination can be evaluated as an absolute margin and/or a ratio between amplitudes of the primary and secondary characteristics. The signal discrimination can also be evaluated based at least in part on a calculated mean and standard deviation according to each configuration.

11 Claims, 11 Drawing Sheets

IMPLANTABLE MEDICAL DEVICE WITH AUTOMATIC SENSING ADJUSTMENT

CROSS-REFERENCE TO RELATED APPLICATIONS

This application is a continuation of U.S. patent application Ser. No. 11/366,929, now U.S. Pat. No. 7,610,090, filed Mar. 1, 2006, titled "Implantable Medical Device With Automatic Sensing Adjustment".

FIELD OF THE INVENTION

The invention relates to the field of implantable medical devices (IMDs) and more particularly to systems and methods for automatically evaluating a plurality of sensing configurations and selecting a configuration with improved sensing performance.

BACKGROUND OF THE INVENTION

Implantable cardiac stimulation devices, such as pacemakers and/or cardioverter/defibrillators (ICDs), are widely used to monitor and provide therapy for a variety of cardiac arrhythmias. Implantable cardiac stimulation devices generally include one or more implantable sensing/stimulation leads which are typically implanted such that electrodes are in contact with one or more chambers of the patient's heart so as to sense physiologic signals from the heart corresponding to the cardiac activity as well as to provide therapeutic stimulation to the heart when indicated. The electrodes can be configured for dedicated sensing or delivery of therapeutic stimulation or can perform both functions as indicated.

The leads and electrodes are configured in pacing applications for "unipolar" sensing/stimulation when a single electrode of the lead acts as one electrical node with a conductive housing or can of the implantable stimulation device acting as the other electrical node. In both pacing and ICD applications, "bipolar" sensing is employed when separate electrodes of the leads sense between the electrodes themselves rather than between an electrode and a typically more distant case or device housing electrode. Bipolar sensing typically offers the advantage of reduced influence from muscular activity and other far field signals on the signals of interest.

In ICD applications, bipolar sensing can be further distinguished between what is often called "true" bipolar and integrated bipolar sensing. True bipolar sensing is performed between a pair of electrodes, one of which is often strictly a pacing or sensing electrode, e.g. is not used for shock delivery. In integrated bipolar sensing, sensing is performed between a coupled electrode pair (typically the ring and shocking coils) and a small tip electrode. In ICD applications, the terms "unipolar sensing" are often used differently than in pacing applications. In the ICD case, "unipolar sensing" typically means sensing from the tip to the RV coil.

Bipolar configurations are preferred in many applications as they provide more localized sensing adjacent the patient's heart tissue. However, as the sensing electrodes are relatively small and positioned close together, a true bipolar sensing configuration can return a relatively small difference between the sensed magnitudes of the R and T waves such that the implantable stimulation device can more readily erroneously double count on the patient's T waves (FIGS. 9A and 9C) leading to an erroneous tachycardia determination which can result in the delivery of unnecessary and painful shocks. The "integrated bipolar" configuration (as well as the ICD unipolar configuration) generally can provide a significantly increased amplitude of the sensed R wave without proportionately increasing the sensed T wave and thus significantly reduce the likelihood of the implantable cardiac stimulation device double counting on the patient's cardiac activity (FIG. 9B).

However, as one electrode of the integrated bipolar configuration typically has a relatively large surface area and extends much closer to the patient's atrium in an implanted condition, the integrated bipolar configuration tends to more strongly sense the P waves which can also present difficulties in accurately counting the true cardiac activity in certain circumstances. Depending upon the particular configuration of lead(s) employed as well as the physiological morphology of the patient and their particular needs for sensing and stimulation, a true bipolar or an integrated bipolar sensing configuration can provide more effective sensing and stimulation. Thus, a clinician will typically evaluate various configurations of lead sensing as well as placement of the lead(s) at the time of implantation and select the one with the best performance.

However, a preferred sensing configuration can change over time, for example due to a changed interrelationship between the patient's physiology and the implantable lead, and it would be desirable to be able to automatically accommodate such changes to select the lead configuration providing sensing with reduced likelihood of, for example, double counting single cardiac events. It would be further advantageous to have this capability without requiring the direct immediate intervention of the clinician, for example, at a subsequent clinical follow-up, e.g. to have the device respond automatically. It would also be desirable to provide additional sensing configurations that might offer more accurate sensing than known configurations.

SUMMARY

In one embodiment, what is described herein is an implantable medical device comprising a plurality of implantable sensing electrodes and a controller receiving signals corresponding to activity of at least one physiologic process according to at least two signal configurations of the plurality of electrodes and wherein the controller automatically evaluates sensing according to each of the signal configurations and selects the signal configuration with more inhibited oversensing for ongoing sensing of the physiologic process.

Another embodiment is a method of sensing physiological signals, the method comprising implanting a medical device with implantable sensors, sensing a physiological parameter having primary and secondary characteristics with at least a first and second configuration of the implantable sensors, quantitatively evaluating by the device the sensing performed under the at least first and second sensor configurations, and automatically selecting the sensor configuration having the largest discrimination between the primary and secondary characteristics for subsequent sensing of the physiologic parameter.

Thus, certain embodiments offer alternative sensor configurations which can offer improved sensing effectiveness in certain applications. Embodiments also offer the ability to automatically evaluate a number of different sensor configurations or processing algorithms performed on sensor configurations and selects the configuration/algorithm with the lowest exposure for erroneous double-counting. Embodiments can be readily provided at relatively low expense to existent hardware configurations. These and other objects and advantages of the invention will become more apparent from the following description taken in conjunction with the accompanying drawings.

DETAILED DESCRIPTION

Reference will now be made to the drawings wherein like numerals refer to like parts throughout. The following description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Figure 1:
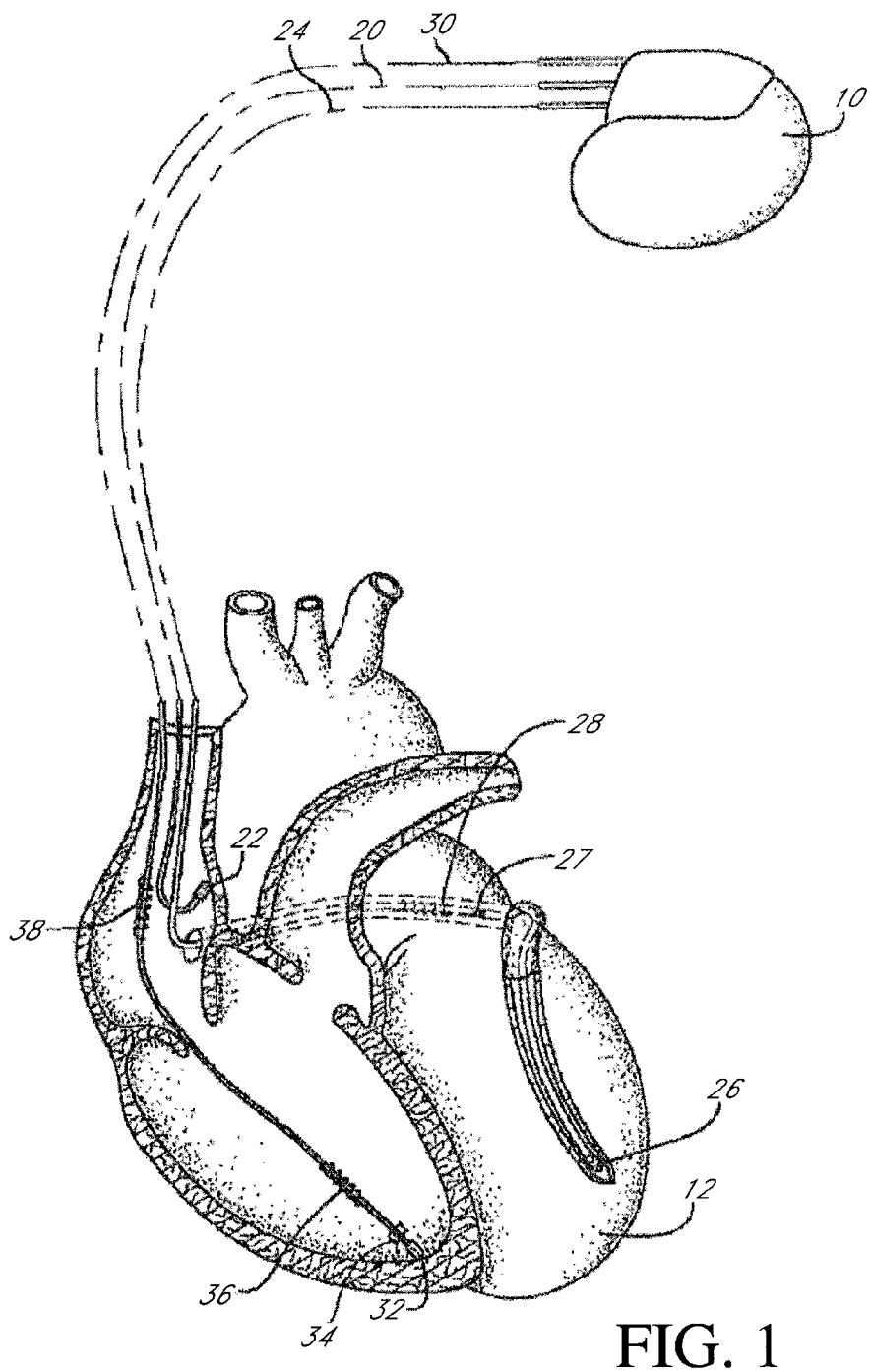
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
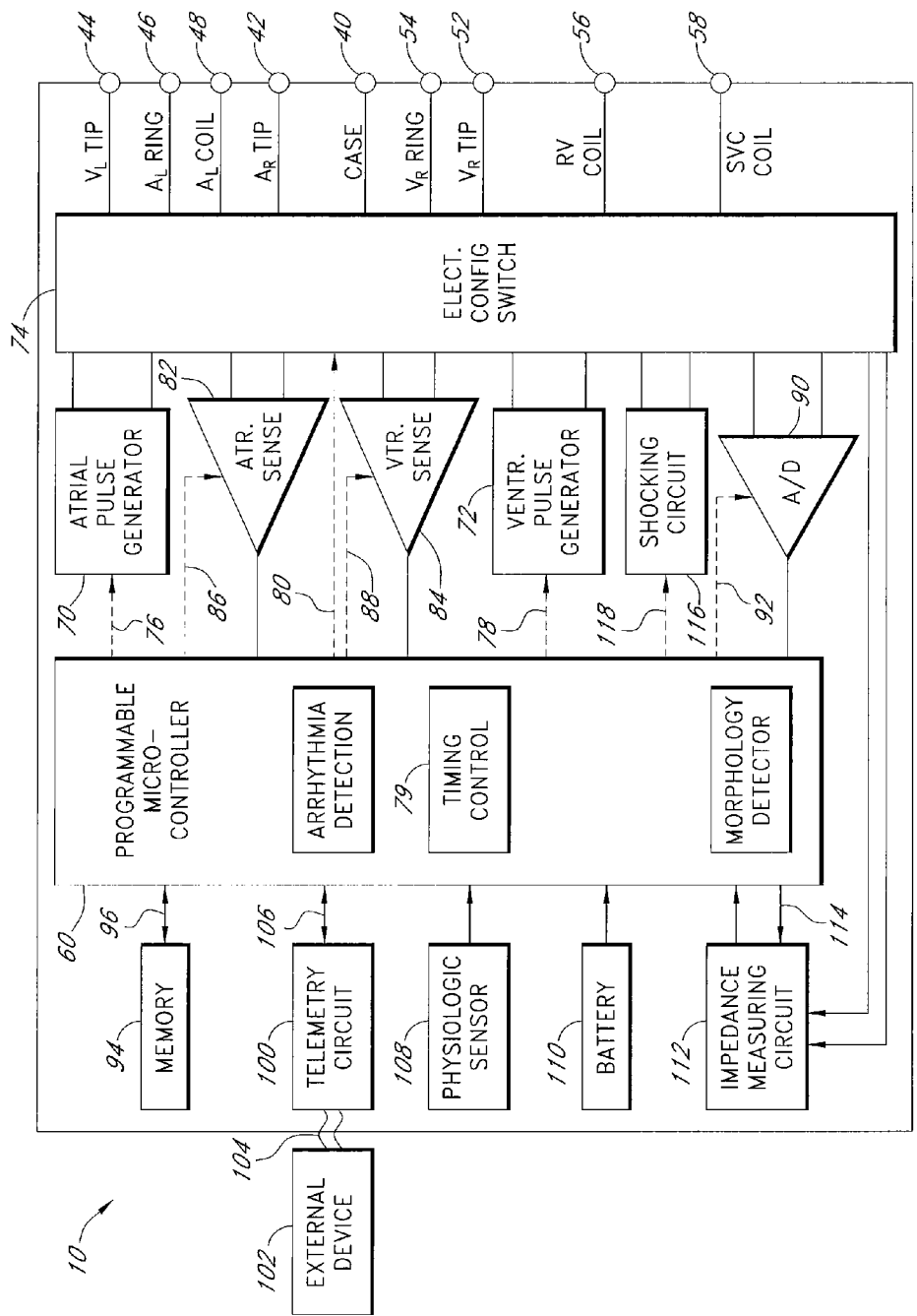
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all pacemaker "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
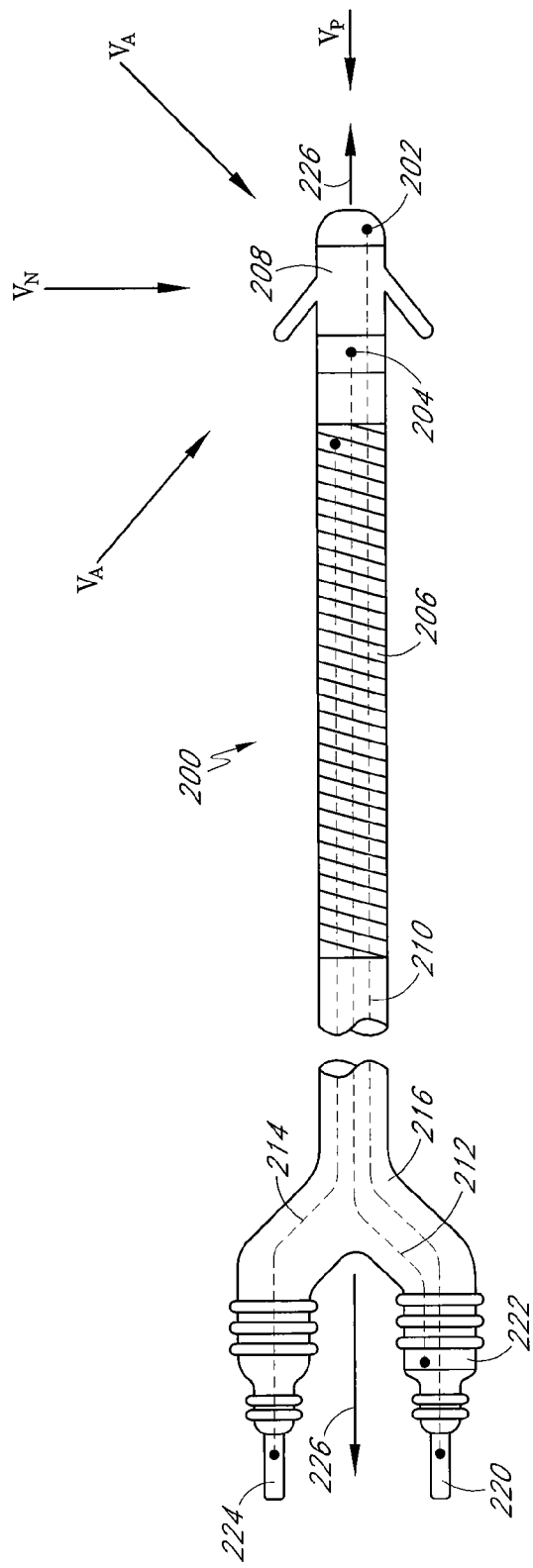
FIG. 3 illustrates one embodiment of an implantable sensing/stimulation lead.

FIG. 3 illustrates one embodiment of an implantable sensing/stimulation lead 200 with a plurality of electrodes suitable for both true bipolar and integrated bipolar sensing as well as delivery of therapeutic stimulation. The lead 200 includes a distally disposed tip electrode 202 and a ring electrode 204 positioned adjacent the tip electrode 202 with a fixation structure 208 interposed therebetween. The fixation structure 208 is configured to secure the lead 200 in place once it is implanted in the patient. The lead 200 further comprises a relatively large area coil electrode 206 with a distal end of the coil electrode 206 extending adjacent the ring electrode 204 and with the opposite end of the coil electrode 206 extending approximately away from the distal end of the lead 200. Each of the tip 202, ring 204, and coil 206 electrodes are connected to conductors 210, 212, 214 respectively to conduct signals from the electrodes 202, 204 and 206 as well as to conduct therapeutic stimulations to the electrodes 202, 204, 206. The electrodes 202, 204, 206 as well as the conductors 210, 212, 214 are electrically isolated from each other by insulator material 216 which provides both electrical insulation as well as structural support for the lead 200. The conductors 210, 212, 214 are terminated with connectors 220, 222, 224 respectively to facilitate communication between the electrodes 202, 204, 206 and internal circuitry of an implantable stimulation device 10.

FIG. 3 also illustrates schematically certain difficulties in sensing with such a lead 200 which is addressed by embodiments of the invention as will be described in greater detail below. More particularly, as previously noted the lead 200 would typically be implanted such that the electrodes 202, 204, 206 are in electrical communication with the patient's heart 12. A physician will implant the lead 200 taking into account the structural morphology of the individual patient's heart 12, the sensing and stimulation indications for the particular patient, the characteristics of the particular lead 200, available structures and methods for fixing the lead 200 in place, as well as other considerations particular to the unique application of the individual patient and implantable device 10.

The lead 200 will be sensing time varying electrical signals which propagate in three dimensional space through the patient's body. The particular vectors along which the time varying signals propagate, as well as their spatial orientation with the major axis 226 of the lead 200 will typically vary from patient-to-patient and can even vary to some extent over time within a particular patient. Thus the relative incidence of a physiological signal sensed by the lead 200 can vary from an aspect wherein the sensed waveform has a substantially parallel incidence angle to the major axis 226 of the lead 200 indicated in FIG. 3 by the incoming signal $V_P$ to an orientation wherein the incident physiological signal is substantially perpendicular or normal to the major axis 226 indicated in the FIG. 3 by the incoming waveform $V_N$. Of course, in many applications, the incident angle of the incoming physiological signal would lie somewhere between a parallel and a normal incident angle and this generally more common circumstance is illustrated by the incoming physiological signals indicated by $V_A$.

As the incoming physiological signals are time varying in three dimensional space, the particular incidence angle of the physiologic signals, particularly their orientation with respect to the electrodes 202, 204, 206, will affect sensed potential differences between these electrodes. For example, in the case wherein the physiological signal is incident substantially perpendicular or normal to the major axis 226 as the incoming physiological signal impinges upon the electrodes 202, 204, 206, although the physiological signal can exhibit relatively pronounced potential variations in space and time, a substantially equipotential wavefront will be presented to each of the electrodes 202, 204, 206 as the physiologic signal propagates past the lead 200. This arrangement would present significant difficulties in accurately sensing any potential difference between pairs of the electrodes 202, 204, 206.

In contrast, in the circumstance wherein the incident physiological signal is aligned substantially parallel with the major axis 226, for example, as indicated by the incoming physiologic signal waveform $V_P$, bipolar sensing between pairs of the electrodes 202, 204, 206 can much more readily sense potential differences in the incident physiologic signal as it passes along the major axis 226 as the individual electrodes 202, 204, 206 are distributed in space along the major axis 226 and thus will be presented with potential differences as the incident physiological signal waveform propagates along the lead 200. Of course, the circumstance wherein the physiologic signal is incident along an angle between the normal and parallel will present a case intermediate between the extremes of a normal incidence and a parallel incidence with respect to the degree of potential differentiation presented by the time varying spatial waveform between pairs of the electrodes 202, 204, 206.

As previously described, true bipolar refers to applications wherein sensing is performed between a pair of electrodes, such as the tip electrode 202 and the ring electrode 204. The lead 200 can also be used to sense in an integrated bipolar fashion wherein the ring 204 and coil 206 electrodes are coupled together to form a reference for sensing with respect to the tip electrode 202. True bipolar sensing can offer the advantage of more precise sensing as the tip 202 and ring 204 electrodes are relatively small and thus provide more precise localized potential sensing, but in certain applications at the risk of increased double-counting errors. In one embodiment, a true "ICD unipolar" configuration, the sensing is from the tip 202 to the coil 206.

As previously mentioned, sensing with an implantable cardiac stimulation device, such as the device 10, can take place under a plurality of sensing configurations. As used herein, sensing configurations can be a function of the physical arrangement of a particular lead and/or a function of the manner in which signals between multiple electrodes are processed and analyzed. For example, a number of different sensing configurations can be effected with respect to sensing with the electrodes 22, 26, 27, 28, 32, 34, 36, and/or 38.

Figure 4:
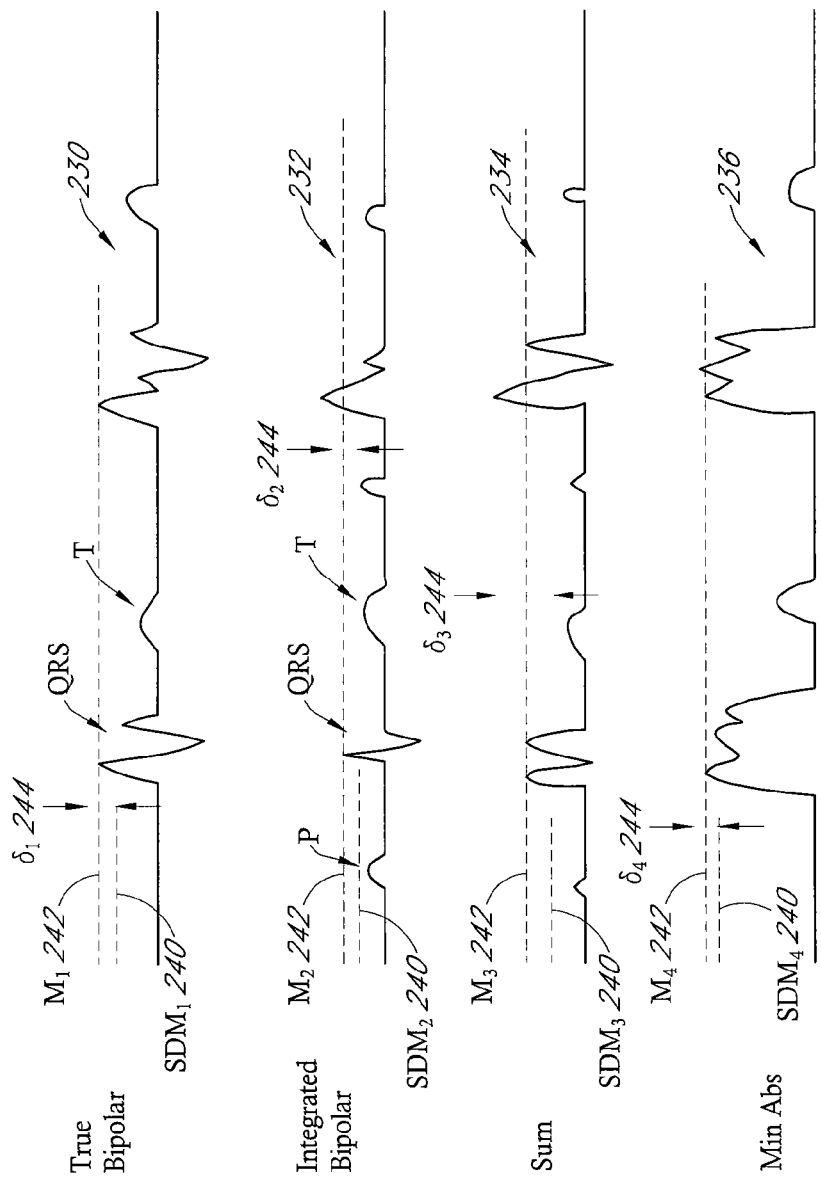
FIG. 4 illustrates embodiments of physiological parameters sensed under different sensing configurations and processed signals obtained therefrom.

FIG. 4 is a schematic illustration of sensing performed under various sensing configurations and embodiments of processing of the sensed signals to reduce likelihood of over counting the sensed physiological signals. In this embodiment, sensing according to a first configuration 230 comprising a true bipolar arrangement and also in a second configuration 232 comprising an integrated bipolar arrangement is illustrated in this embodiment corresponding to sensed cardiac activity as in an intracardiac electrogram (IEGM). The sensing according to the first configuration 230 is characterized by a relatively jagged QRS complex and a more rounded T wave. The sensing according to the second configuration 232 is characterized by the presence of a preceding P wave before the QRS complex and a T wave which is of lower amplitude than the T wave as measured according to the first configuration 230. The varied relative locations of the sensing electrodes 22, 26, 27, 28, 32, 34, 36, and/or 38 in various implementations of sensing configurations results in greater or lesser sensitivity to particular aspects of cardiac activity, such as indicated by the QRS complex, P waves, T waves, etc.

FIG. 4 also illustrates waveforms corresponding to a first processed sensed signal 234 as well as a second processed sensed signal 236. In one embodiment, the first processed signal 234 corresponds to a combination or point-by-point summation of the sensed signals of the first configuration 230 and the second configuration 232. Thus, in this embodiment, the first processed sensed signal 234 has the common characteristics between the sensing of the first configuration 230 and second configuration 232, e.g., the P waves from the second configuration 232 as well as the relatively high amplitude T waves from the first configuration 230. The first processed sensed signal 234 can be considered to define an additional sensing configuration.

In this embodiment, the second processed sensed signal 236 is obtained by further processing of the sensing of the first and second configurations 230, 232 and in one particular embodiment, according to what will be referred to as the minimum absolute value function (MINABS). In this embodiment, the second processed sensed signal 236 is obtained by taking the absolute value of both of the sensed signals according to the first configuration 230 and second configuration 232 and then at each point in time defining the value of the second processed sensed signal 236 as the lesser of the absolute value of the sensed signal according to the first 230 or second 232 configuration. Thus, in this embodiment, the second processed sensed signal will have the P wave substantially removed as the signal according to the first configuration 230 will have a relatively low amplitude signal for the P wave and the second processed sensed signal 236 will also have the lower amplitude T wave of the second 232 configuration. The second processed sensed signal 236 will also have a relatively strong R wave corresponding to the absolute value of the QRS complexes of the first 230 and second 232 configurations. Thus, as can be seen in FIG. 4, the second processed sensed signal 236 exhibits a particularly high amplitude and distinct processed QRS signal complex. The second processed sensed signal 236 can be considered to define yet another sensing configuration. All of the signals according to the first and second configurations 230, 232 as well as the first and second processed sensed signals 234, 236 can be considered cardiac signals representative of different perspectives or measures of the patient's cardiac activity.

Figure 5:
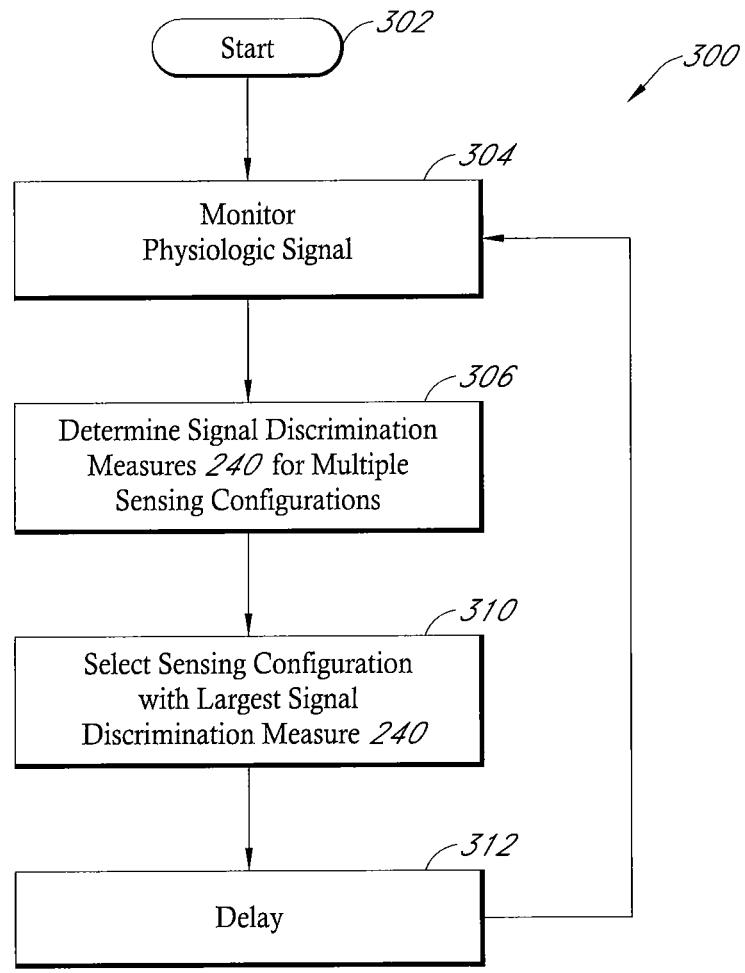
FIG. 5 is a flow chart of one embodiment of a method of automatic sensing adjustment.

FIG. 5 illustrates embodiments of a method and system 300 for automatically evaluating the sensed signals of multiple configurations as well as multiple processed signals obtained from the sensed signals to automatically select a configuration or processing of signals configuration with improved sensing performance. More particularly, following a start state 302, in state 304 one or more physiologic signals are monitored in multiple configurations, such as the first 230 and second 232 configurations previously described. The monitoring of state 304 preferably proceeds for a period of time sufficient to obtain a representative sample of multiple iterations of the physiologic process of interest. For example, in certain embodiments, the monitoring of state 304 would proceed for several minutes to provide monitoring of numerous cardiac cycles.

Following the monitoring of state 304, in a state 306 signal discrimination measures 240 are determined for the multiple sensing configurations monitored in the state 304. The signal discrimination measures 240 provide indications of the relative ease with which particular physiological events, for example the cardiac activity indicated by a QRS complex, can be readily discriminated and accurately determined with reduced likelihood for false positives and false negatives (double counting, undercounting, and the like). The signal discrimination measures 240 can be indicative of the relative amplitude and/or duration of signal characteristics corresponding to a particular physiologic event as compared to the characteristics of the signal absent the physiological event as well as provide indications for the repeatability or variability of the signal. Generally, a larger relative amplitude of a signal corresponding to a physiological event compared to the magnitude of the signal absent the physiologic event combined with a higher degree of repeatability/lower degree of variability would provide larger signal discrimination measures 240 of signals having characteristics wherein the physiologic event of interest can be more readily discriminated.

In one particular embodiment, the determination of signal discrimination measures 240 in the state 306 comprises evaluating the multiple configurations for monitoring physiologic signals of state 304 for multiple iterations of the underlying physiologic process and determining a mean 242 and a corresponding standard deviation 244 from the mean 242. In one particular embodiment, as illustrated in FIG. 4, a mean 242 and a standard deviation 244 are determined for each of the sensed signals according to the first configuration 230, the sensed signals accordingly to the second configuration 232, the first processed sensed signal 234 and the second processed sensed signal 236. In this particular embodiment, the signal discrimination measure 240 for each of the sensed signals or processed sensed signals is defined as the corresponding mean minus one standard deviation (equal to M−Δ). In other embodiments, the signal discrimination measure 240 comprises a ratio or absolute difference between the observed peak amplitudes of the QRS complexes and other potentially confounding events, such as T and/or P waves.

As can be seen graphically in FIG. 4, the signal discrimination measures 240 for the first configuration 230 and for the second configuration 232 are relatively low due to a relatively low mean 242 of the peak amplitudes with a relatively large degree of variability, e.g. a relatively large standard deviation 244. The signal discrimination measure 240 for the first processed sensed signal 234 is also relatively small because, while in this embodiment the mean peak amplitude 242 is relatively large, the first processed sensed signal 234 exhibits a relatively large degree of variability corresponding to a relatively large standard deviation 244 and thus the signal discrimination measure 240 defined in this embodiment as equal to the mean 242 minus one standard deviation 244 is relatively low. However, the signal discrimination measure 240 for the second processed sensed signal 236 is relatively large due to the relatively large amplitude of the mean of the peak amplitude 242 and a corresponding relatively low degree of variability, e.g., a relatively small standard deviation 244. Thus the signal discrimination measure 240 for this processed signal 236 is relatively large.

A visual comparison of the waveforms illustrated in FIG. 4 corresponding to the sensed signal of the first 230 and second 232 configurations as well as the first 234 and second 236 processed sensed signals reveals that the waveform of the second processed sensed signal 236 more readily discriminates the corresponding physiologic activity of the cardiac activity corresponding to the QRS complex from the P and T waves. Thus, each cardiac cycle can be more readily identified with the second processed sensed signals 236 than in the other three waveforms or configurations, in this embodiment.

According to certain embodiments, the system and method 300 make this determination quantitatively in an automatic manner. Thus, the larger signal discrimination measure 240 indicates that the second processed sensed signal 236 can be evaluated by the device 10 with reduced likelihood, for example, of double counting the corresponding physiological process of the QRS complex as the mean peak amplitude 242 is relatively large and exhibits a relatively low degree of variability as indicated by the relatively low standard deviation 244.

Thus, following in a state 310, the sensing configuration with the largest signal discrimination measure 240 is selected for subsequent sensing. However, it will be appreciated that in other embodiments, other waveforms would present the larger signal discrimination measure 240, such as the first configuration 230, the second configuration 232, or the first processed sensed signal 234 as well as other possible sensing configurations. Also, as previously mentioned, the sensing characteristics with a particular sensing configuration are subject to change over time and thus, in this embodiment, following the selection of state 310, a delay period 312 occurs followed by a repetition of the system and method 300 wherein the monitoring of state 304, the determination of state 306, and the selection of state 310 are repeated for a possible change in the interaction between the patient and the implantable device 10 indicating selection of a different sensing configuration.

Figure 6:
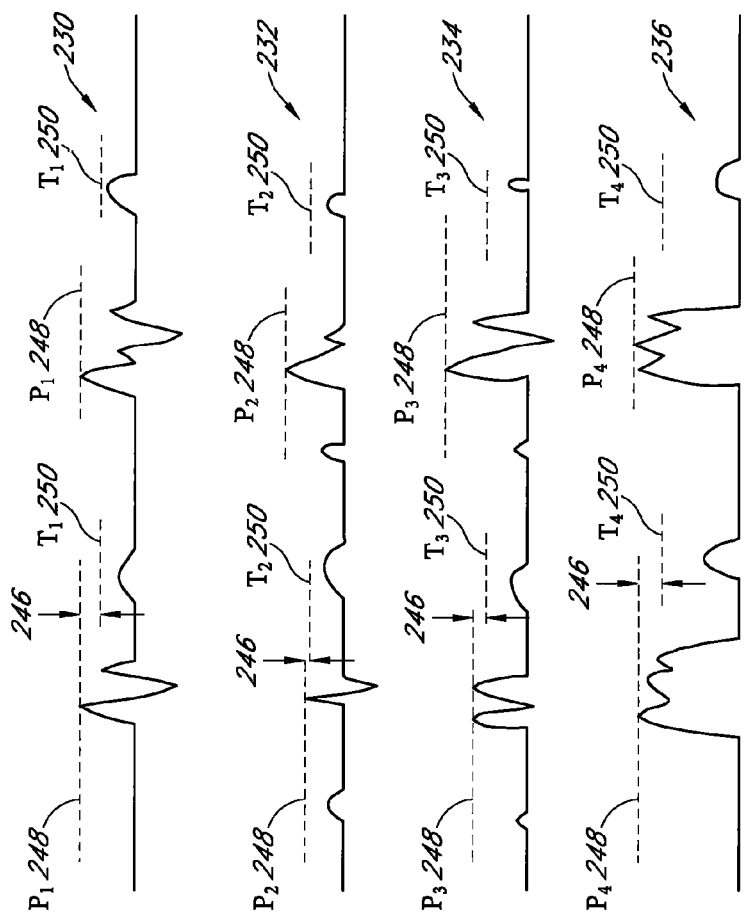
FIGS. 6 and 7 illustrate further embodiments of sensing physiological parameters under multiple configurations and adjusting the sensing.
Figure 7:
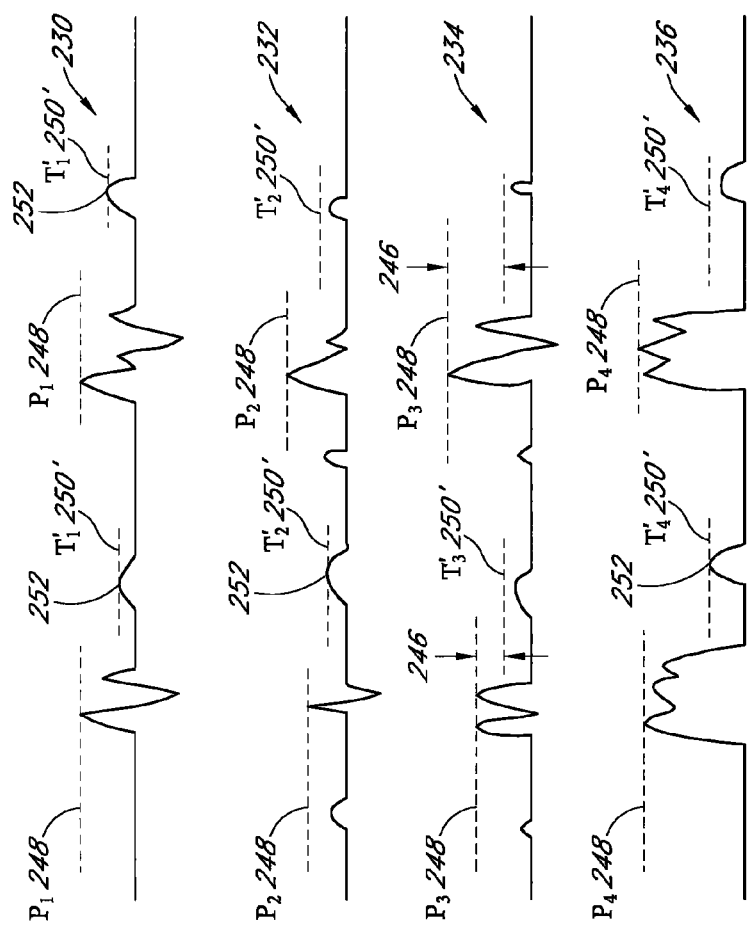

FIGS. 6 and 7 illustrate waveforms of sensing according to a first 230 and second 232 configurations, as well as first 234 and second 236 processed sensed signals. FIGS. 6 and 7 also illustrate sensed signal peaks $P_N$ 248 for multiple cycles of a physiological parameter, as well as thresholds $T_N$ 250 associated with each of the signal peaks $P_N$ 248. In this embodiment, the thresholds $T_N$ 250 are varied and evaluated with respect to the corresponding signal peaks $P_N$ 248 according to embodiments of a system and method 350 to determine a sensing safety margin 246.

More particularly, FIG. 6 illustrates embodiments of waveforms corresponding to the sensing performed according to the first 230 and second 232 configurations, as well as first 234 and second 236 processed sensed signals obtained therefrom. With each of these waveforms is associated a corresponding signal peak $P_{1-4}$ 248, respectively, with a corresponding threshold $T_{1-4}$ 250 associated therewith. The signal peak $P_N$ 248 corresponds generally to the peak amplitude associated in this embodiment with the peak magnitude of the QRS complex. As previously noted, a goal of certain embodiments is to improve accuracy of sensing of physiologic activity, for example, cardiac activity, and to obtain an accurate rate or count over time of this activity with reduced errors due to, for example, double counting of a T-waves erroneously interpreted as corresponding to a QRS complex of a separate cycle.

Thus, in these embodiments, the thresholds $T_N$ 250 are preferably set in such a manner such that when the signal amplitude exceeds the threshold, the device 10 accurately interprets this excursion as corresponding to an occurrence of the physiologic process of interest with reduced instances of secondary signals, such as T-waves, also exceeding the threshold $T_N$ 250, thus possibly leading to an erroneous interpretation of the secondary signal as corresponding to an occurrence of the primary signal and thus possibly leading to an erroneous double count of the activity. The threshold $T_N$ 250 is also preferably set to provide a larger tolerance or sensing safety margin 246 between the peak $P_N$ 248 and the threshold $T_N$ 250 to provide wider accommodation of variation in signal amplitude while still inhibiting the erroneous double counting of secondary signals. As can be seen in FIG. 6, for each of the first 230 and second 232 sensing configurations, as well as the first 234 and second 236 processed sensed signals, the corresponding peaks $P_{1-4}$ 248 and thresholds $T_{1-4}$ 250 provide a sensing safety margin 246 and desirably avoid secondary signals, such as T-waves, from exceeding the thresholds $T_{1-4}$ 250 and thus avoid the undesirable double counting.

FIG. 7 illustrates a subsequent step in the system and method 350 wherein the thresholds have been adjusted lower as indicated by $T'_{1-4}$ 250', respectively. As can be further seen in FIG. 7, according to the first configuration 230, incidences of double counting 252 occur on both cycles of the physiologic activity as the secondary characteristics of the physiologic process return a signal amplitude in excess of the threshold $T'_1$ 250'. According to the second configuration 232, the first cycle of the physiologic activity also returns an incident of a double count 252, however, for the second cycle according to the second configuration 232, the secondary characteristic has an amplitude that does not exceed the revised threshold $T'_2$ 250'. A similar circumstance also exists in this embodiment for the second processed sensed signal 236 with respect to the threshold $T'_4$ 250. However, for the first processed sensed signal 236, both cycles of the physiologic activity have secondary characteristics which do not return a signal amplitude in excess of the threshold $T'_3$ 250' and thus in this embodiment, the sensing safety margin 246 of the first processed sensed signal 234 would be selected as offering a larger tolerance between the respective peaks $P_3$ 248 and the thresholds $T'_3$ 250' while also avoiding the undesirable incidences of double counts 252 occurring according to the sensing of the first configuration 230, the second configuration 232, and the second processed sensed signal 236. In various embodiments, the threshold $T_N$ 250 referred to above can comprise a set value and/or can also comprise a function of the respective signal peak $P_N$ 248, such as a percentage of the signal peak, or a fixed value less than the signal peak $P_N$ 248.

Figure 8:
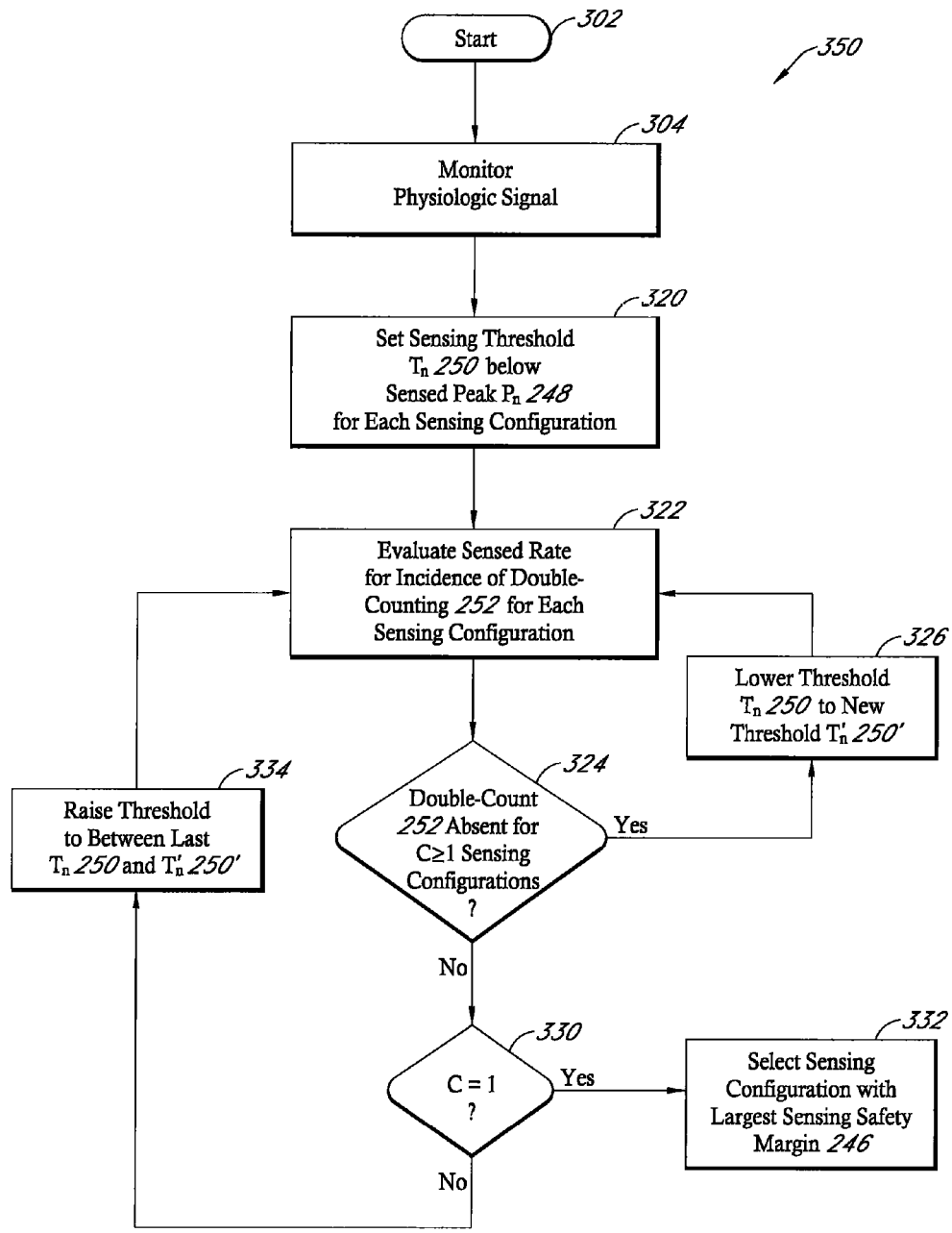
FIG. 8 is a flowchart of another embodiment of automatically adjusting sensing of an implantable medical device.
Figure 9A:
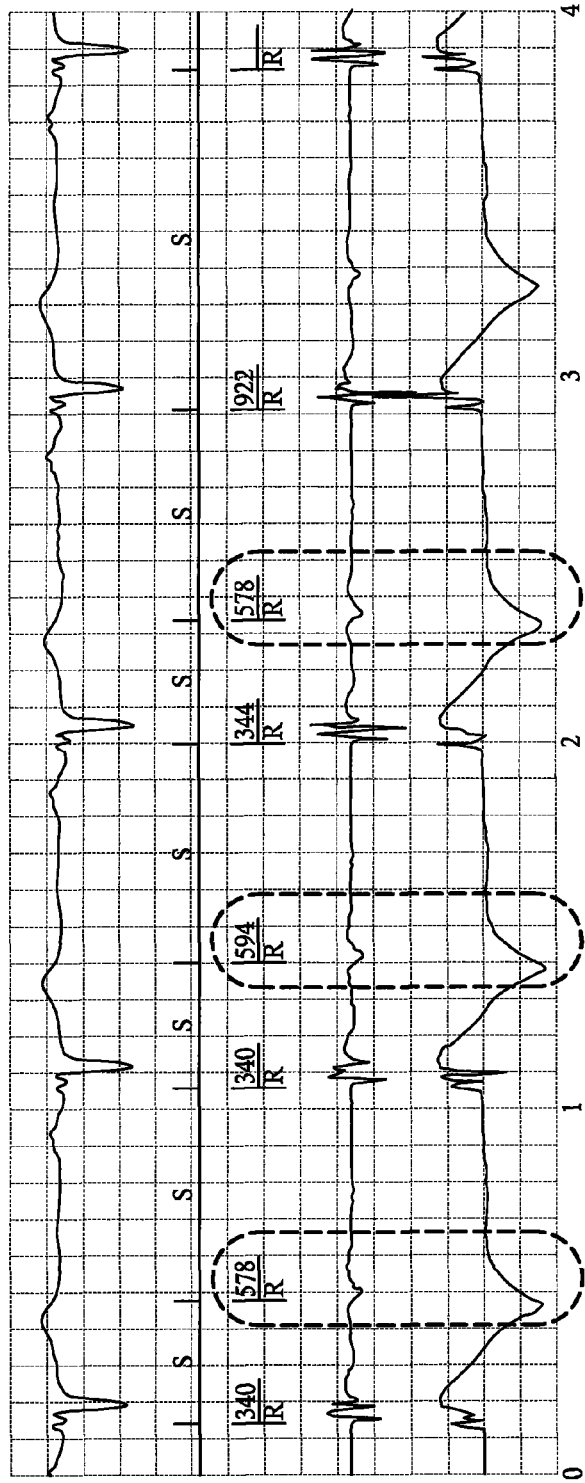
FIGS. 9A-9C are sample waveforms of sensing performed with true bipolar and integrated bipolar configurations showing instances of double counting.
Figure 9B:
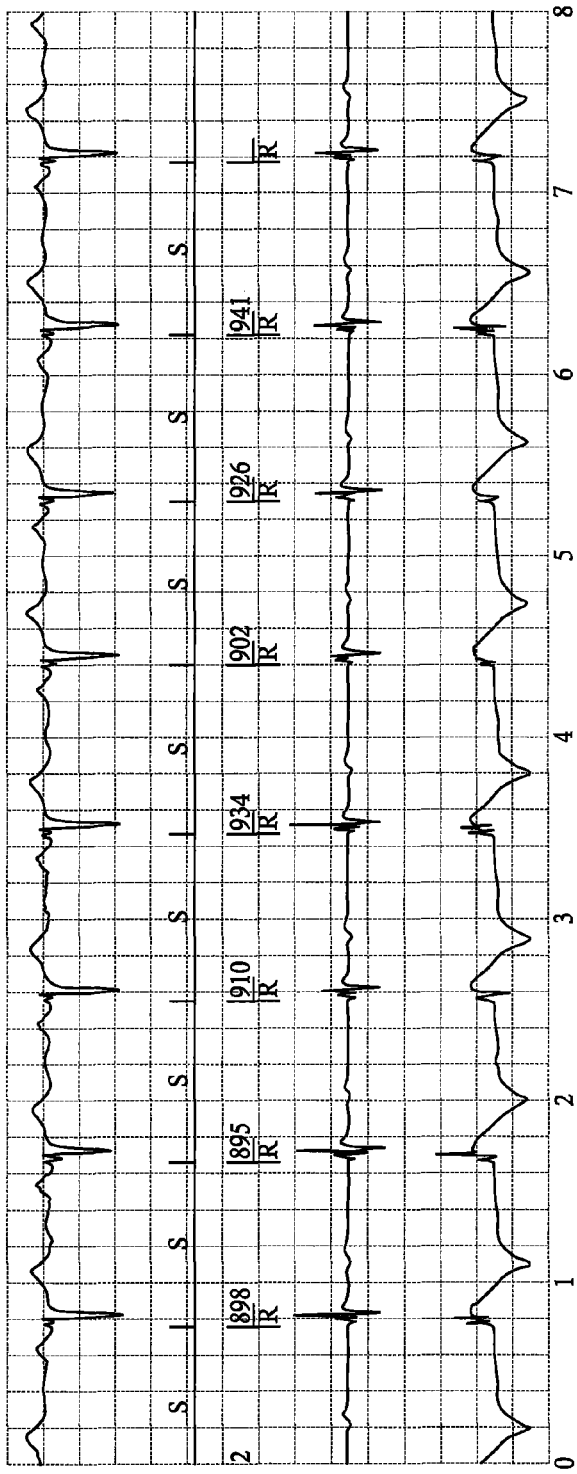
Figure 9C:
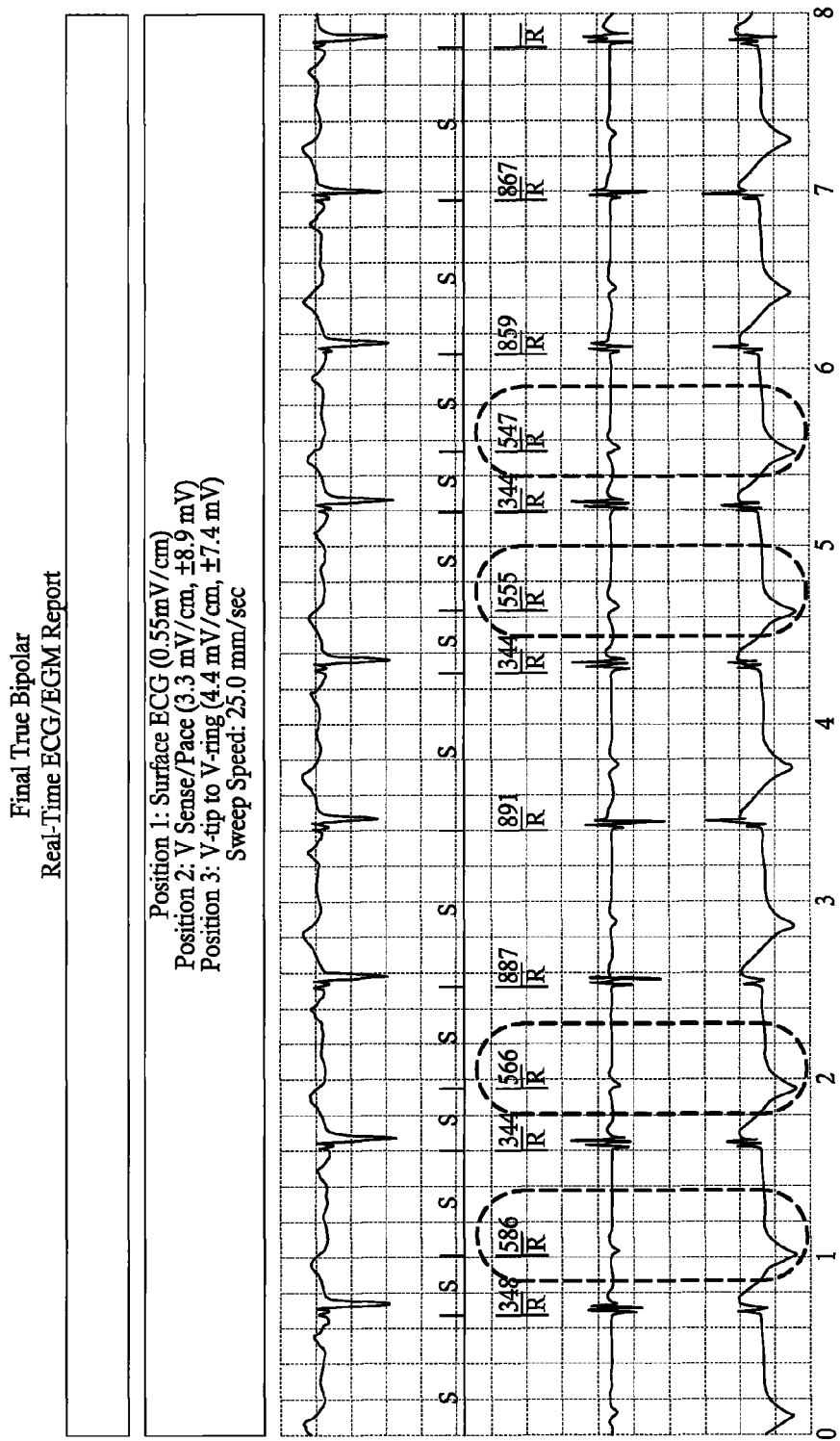

Thus, according to one embodiment as illustrated in FIG. 8, a system and method for automatic sensing adjustment 350 begins in a state 302 substantially similar to the state 302 of the system and method 300 and proceeds to a monitoring state 304 wherein sensing performed according to multiple configurations or processing of the sensed signals occurs substantially similarly to that previously described in the system and method 300. This is followed by a state 320 wherein the sensing threshold $T_N$ 250 is set below the corresponding sensed signal peak $P_N$ 248 for each of the sensing configurations and/or processing. This is followed by a state 322 wherein the physiologic signal as sensed and/or processed is evaluated to determine the rate and further evaluated for incidents of double counting 252 for each of the sensing configurations and/or processing of the sensing. Incidents of double counting 252 would generally be indicated by an abrupt increase in the determined rate absent other indicators corroborating a true physiologically based increase in the parameter. Incidents of double counting 252 would also be indicated by an aperiodic pattern to the observed signal peaks, e.g., alternating periods of a relatively high rate with periods of a relatively low rate. Other algorithms for determination of double counting or over sensing will be known and understood by one of ordinary skill in the art and could be implemented in the system and method 300, 350 without detracting from the scope of the invention.

Following from the evaluation of state 322 is a decision state 324 wherein each of the sensing configurations and processing of the sensing is examined for presence of double counting and the decision of state 324 comprises a determination whether the double counts 252 are absent for one or more of the sensing configurations and/or processing(s) of the sensing. If the determination of decision state 324 is affirmative, e.g., that one or more of the sensing configurations and/or processing is proceeding absent double counting 252, a state 326 occurs wherein the threshold $T_N$ 250 is lowered to a new threshold $T'_N$ 250' and the evaluation of state 322 is repeated. Thus, the method and system 350 iteratively set the threshold $T_N$ 250 to a more aggressive threshold $T'_N$ 250' to increase the sensing safety margin 246 for the respective configuration or processing.

If the determination of decision state 324 is negative, e.g., that double counting 252 is occurring for all but one or more of the sensing configurations or processing, a decision state 330 follows wherein an evaluation is made as to whether the threshold $T_N$ 250 has been set aggressively enough such that only a signal sensing configuration or processing of the sensing is proceeding absent double counting 252. If the evaluation of state 330 is affirmative, the system and method 350 determine that the sensing configuration or processing with the largest sensing safety margin 246 has been determined and this configuration is selected in state 332 to provide a sensing configuration with the largest sensing safety margin 246. If the determination of state 330 is negative, e.g., that a single sensing configuration or processing has not been identified, a state 334 follows wherein the threshold is raised to between the last two thresholds $T_N$ 250 and $T'_N$ 250' so as to further refine the thresholds for each of the sensing configurations and/or processings.

Thus, embodiments of the invention provide novel arrangements for sensing signals, such as by processing signals obtained via different sensor configurations into a third processed signal combining the two according to certain functions. Embodiments also provide systems and methods for automatically evaluating the performance of various sensing configurations and the processing of those configurations which result in additional processed configurations. The evaluation is used to select an improved configuration for subsequent sensing on either a predictive basis based on the analysis or on an empirical basis by comparing the performance of the multiple configurations, for example with respect to double-counting events. The various embodiments can be readily implemented with otherwise conventional implantable devices 10 via relatively inexpensive software upgrades thus significantly increasing the utility of the devices 10 at relatively low cost.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable medical device comprising:
a plurality of electrodes;
circuitry configured to arrange the plurality of electrodes in a first sensing configuration and a second sensing configuration; and
a controller configured to:
receive a first cardiac electrical activity signal from the first sensing configuration and a second cardiac electrical activity signal from the second sensing configuration;
combine the first cardiac electrical activity signal and the second cardiac electrical activity signal in one or more ways to create corresponding one or more processed cardiac electrical activity signals; and
evaluate the first cardiac electrical activity signal, the second cardiac electrical activity signal and the one or more processed cardiac electrical activity signals to select a corresponding one of the signals for subsequent processing of cardiac electrical activity;
wherein each of the first cardiac electrical activity signal, the second cardiac electrical activity signal and the one or more processed cardiac electrical activity signals exhibits primary and secondary characteristics and the controller is configured to evaluate by being further configured to:
calculate for each signal, a discrimination measure between the sensed amplitudes of their respective primary and secondary characteristics; and
select the signal corresponding to the largest discrimination measure as the one that provides more inhibited oversensing; and
wherein the controller is configured to calculate a discrimination measure by being further configured to calculate a mean, a corresponding standard deviation and a value of mean minus one standard deviation, for each signal.

2. The device of claim 1 wherein the first sensing configuration comprises a true bipolar arrangement of two electrodes and the second sensing configuration comprises an integrated bipolar arrangement of three electrodes.

3. The device of claim 1 wherein the device periodically evaluates the first cardiac electrical activity signal, the second cardiac electrical activity signal and the one or more processed cardiac electrical activity signals to select a corresponding one of the signals for subsequent processing of cardiac electrical activity.

4. The device of claim 1 wherein the discrimination measure correspond to one or more of a relative amplitude and a duration of a characteristic of a signal.

5. The device of claim 1 wherein the controller is configured to combine the first cardiac electrical activity signal and the second cardiac electrical activity signal by being further configured to add the signals together.

6. An implantable medical device comprising:
   a plurality of electrodes;
   circuitry configured to arrange the plurality of electrodes in a first sensing configuration and a second sensing configuration; and
   a controller configured to:
     receive a first cardiac electrical activity signal from the first sensing configuration and a second cardiac electrical activity signal from the second sensing configuration;
     combine the first cardiac electrical activity signal and the second cardiac electrical activity signal in one or more ways to create corresponding one or more processed cardiac electrical activity signals; and
     evaluate the first cardiac electrical activity signal, the second cardiac electrical activity signal and the one or more processed cardiac electrical activity signals to select a corresponding one of the signals for subsequent processing of cardiac electrical activity;
   wherein the controller is configured to combine the first cardiac electrical activity signal and the second cardiac electrical activity signal by being further configured to:
     at points in time of the first cardiac electrical activity signal and the second cardiac electrical activity, take the absolute value of the signal; and
     at each point in time of the signals, define the value of the processed signal as the lesser of the absolute value of the first cardiac electrical activity signal and the second cardiac electrical activity.

7. A method of selecting a signal for use in the processing of cardiac electrical activity:
   arranging a plurality of electrodes in a first sensing configuration and a second sensing configuration;
   receiving a first cardiac electrical activity signal from the first sensing configuration and a second cardiac electrical activity signal from the second sensing configuration;
   combining the first cardiac electrical activity signal and the second cardiac electrical activity signal in one or more ways to create corresponding one or more processed cardiac electrical activity signals; and
   evaluating the first cardiac electrical activity signal, the second cardiac electrical activity signal and the one or more processed cardiac electrical activity signals to select a corresponding one of the signals for subsequent processing of cardiac electrical activity;
   wherein each of the first cardiac electrical activity signal, the second cardiac electrical activity signal and the one or more processed cardiac electrical activity signals exhibits primary and secondary characteristics and evaluating the signals comprises:
     calculating for each signal, a discrimination measure between the sensed amplitudes of their respective primary and secondary characteristics; and
     selecting the signal corresponding to the largest discrimination measure as the one that provides more inhibited oversensing; and
   wherein calculating a discrimination measure comprises calculating a mean, a corresponding standard deviation and a value of mean minus one standard deviation, for each signal.

8. The method of claim 7 wherein the first sensing configuration comprises a true bipolar arrangement of two electrodes and the second sensing configuration comprises an integrated bipolar arrangement of three electrodes.

9. The method of claim 7 further comprising periodically evaluating the first cardiac electrical activity signal, the second cardiac electrical activity signal and the one or more processed cardiac electrical activity signals to select a corresponding one of the signals for subsequent processing of cardiac electrical activity.

10. The method of claim 7 wherein the discrimination measure correspond to one or more of a relative amplitude and a duration of a characteristic of a signal.

11. A method of selecting a signal for use in the processing of cardiac electrical activity:
   arranging a plurality of electrodes in a first sensing configuration and a second sensing configuration;
   receiving a first cardiac electrical activity signal from the first sensing configuration and a second cardiac electrical activity signal from the second sensing configuration;
   combining the first cardiac electrical activity signal and the second cardiac electrical activity signal in one or more ways to create corresponding one or more processed cardiac electrical activity signals; and
   evaluating the first cardiac electrical activity signal, the second cardiac electrical activity signal and the one or more processed cardiac electrical activity signals to select a corresponding one of the signals for subsequent processing of cardiac electrical activity;
   wherein combining the first cardiac electrical activity signal and the second cardiac electrical activity comprises:
     at points in time of the first cardiac electrical activity signal and the second cardiac electrical activity, taking the absolute value of the signal; and
     at each point in time of the signals, defining the value of the processed signal as the lesser of the absolute value of the first cardiac electrical activity signal and the second cardiac electrical activity.

* * * * *